United States Patent [19]
Zegdi et al.

[11] Patent Number: 5,893,886
[45] Date of Patent: Apr. 13, 1999

[54] VASCULAR PROSTHESIS

[75] Inventors: Rachid Zegdi, Cachan; Jean-Noël Fabiani, Paris, both of France

[73] Assignee: Association Rene Leriche, Paris, France

[21] Appl. No.: 08/905,934

[22] Filed: Aug. 5, 1997

[30] Foreign Application Priority Data

Aug. 5, 1996 [FR] France .................... 96 09874

[51] Int. Cl.⁶ .................... A61F 2/06
[52] U.S. Cl. .................... 623/1; 606/153; 606/155
[58] Field of Search .................... 623/1, 12; 606/151, 606/154, 155, 156

[56] References Cited

U.S. PATENT DOCUMENTS

| | | |
|---|---|---|
| 3,496,939 | 2/1970 | Odiaga .................... 606/154 |
| 3,974,835 | 8/1976 | Hardy .................... 606/154 |
| 4,352,358 | 10/1982 | Angelchik . |
| 4,523,592 | 6/1985 | Daniel . |
| 4,552,148 | 11/1985 | Hardy .................... 606/154 |
| 4,693,249 | 9/1987 | Schenck et al. . |
| 4,766,898 | 8/1988 | Hardy .................... 606/154 |
| 5,366,462 | 11/1994 | Kaster .................... 606/155 |
| 5,486,187 | 1/1996 | Schenck . |

FOREIGN PATENT DOCUMENTS

WO 87/04915  8/1987  WIPO .

*Primary Examiner*—Michael J. Milano
*Attorney, Agent, or Firm*—Oliff & Berridge PLC

[57] ABSTRACT

The invention relates to a vascular prosthesis capable of being anastomosed onto a tubular pipe with a side opening or an end opening. The prothesis having, at at least one of its ends, an annular sheet delimited by a free edge designed to be positioned in the immediate vicinity of opening in the pipe. The sheet is shaped so that it can be applied around the opening in the pipe against the inside or outside wall of the latter, while preserving its free edge in the immediate vicinity of the periphery of the opening in the pipe.

8 Claims, 2 Drawing Sheets

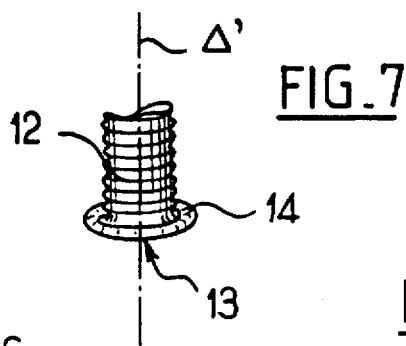
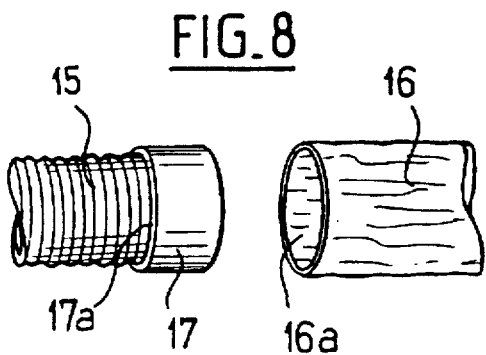
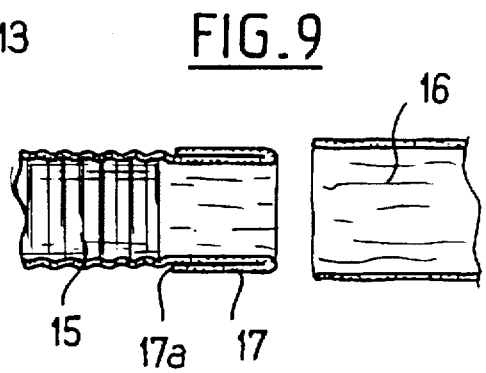
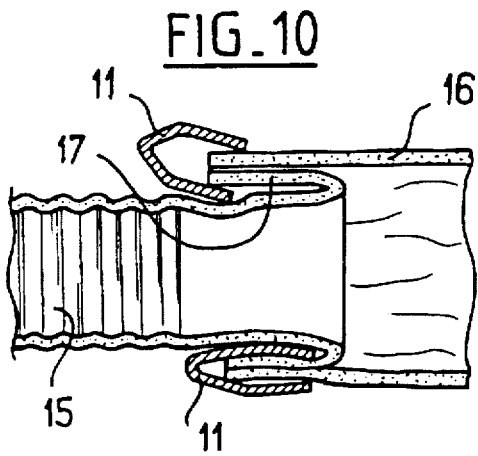
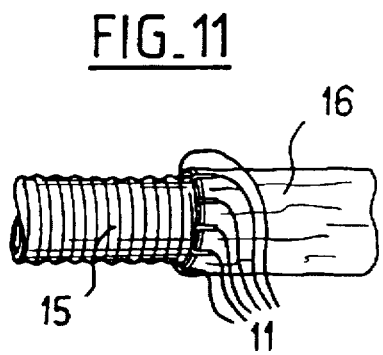
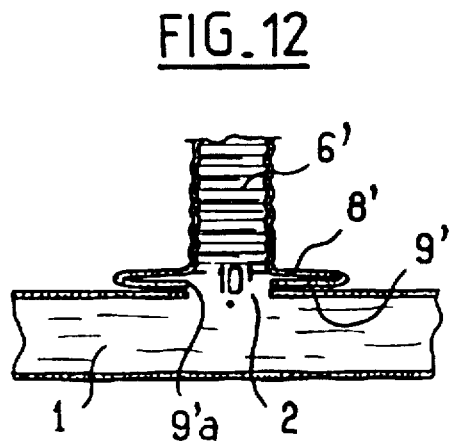
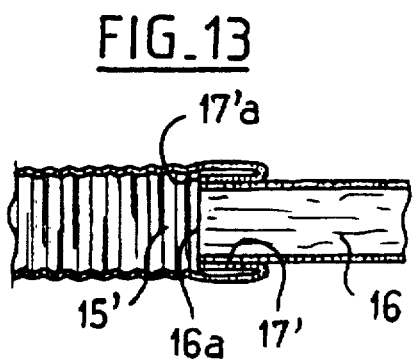

VASCULAR PROSTHESIS

BACKGROUND OF THE INVENTION

1. Field of Invention

The present invention relates to a vascular prosthesis.

2. Description of Related Art

The vascular prostheses used in vascular surgery for treating diseased blood vessels, particularly artery segments, by bypass or by replacement, are essentially cylindrical tubes which, in certain cases, may have branches.

The prostheses in common use today are obtained by weaving or knitting polyester fibers, for example those known as Dacron, the fabric or knit then being coated with a layer of impermeable material. Vascular prostheses made of polytetrafluoroethylene (PTFE) are also used.

An anastomosis of a vascular prosthesis, i.e. placing it in communication with a blood vessel, is traditionally effected by a butt junction of the prosthesis and the vessel, namely by placing their respective openings opposite each other and then edge-suturing these openings. FIG. 1 shows such an anastomosis schematically.

When the diseased portion of a vessel is replaced, an end-to-end anastomosis is made, i.e. the prosthesis is placed in the axial extension of the healthy part of the vessel in place of the diseased portion, which is removed.

In the case of a bypass, an end-to-side anastomosis is made, meaning that the opening in the prosthesis is connected laterally to the vessel, in which a lateral opening has previously been created for the purpose.

In both cases, the prosthesis is sutured to the vessel by a thread.

This surgical technique, which today is well mastered, gives good results.

However, the making of the many suture stitches necessary to create the anastomosis of a prosthesis on a vessel is a skilled operation that must be executed in a small working space, as is the case in particular when the endoscopic technique is used to operate on a vessel through a small opening.

In this case, the time taken by surgery is greatly prolonged, which certain patients may tolerate with difficulty.

It may also be the case that the suturing of a prosthesis onto a diseased artery is very difficult to accomplish, for example when the artery wall is calcified.

The goal of the present invention is to overcome these drawbacks by providing a vascular prosthesis that can be anastomosed onto a vessel without suturing in a particularly simple, rapid, and reliable manner.

SUMMARY OF THE INVENTION

The present invention relates to a vascular prosthesis capable of being anastomosed onto a tubular pipe with a side opening or end opening. The prosthesis having, at at least one of its ends, an annular sheet delimited by a free edge designed to be positioned in the immediate vicinity of the opening in the pipe. The sheet is shaped so that it can be applied around the opening in the pipe against the inside or outside wall of the pipe, while preserving its free edge in the immediate vicinity of the periphery of the opening in the pipe.

As defined by the present invention, an "annular sheet" is understood to be a sheet extending all around the end of the prosthesis, whatever the shape of this sheet.

The prosthesis according to the invention allows the operation of sewing it onto the vessel to be eliminated thanks to the presence of the annular sheet which can be joined to the vessel by clipping or stapling.

In a first embodiment, the prosthesis according to the invention is used to create a side-to-end anastomosis. In this case, it has an annular sheet in the shape of the side part of a cylinder, delimited exteriorly by a peripheral edge corresponding substantially to the intersection of this cylinder with another cylinder, and delimited interiorly by its free edge which defines an orifice that matches the opening in the prosthesis.

The sheet is then connected to the end of the prosthesis by a connecting part which starts at the end of the prosthesis and extends up to the peripheral edge of the sheet Preferably, the connecting part has substantially the same shape as the sheet so that the free end of the sheet is located in the vicinity of the beginning of the connecting part, at the end of the prosthesis.

In a preferred embodiment, the sheet is located outside the connecting part such that the end of the prosthesis passes through the orifice delimited by the free edge of the sheet and extends radially by the connecting part up to the peripheral edge of the sheet, which covers the connecting part.

Such a sheet is placed on a blood vessel having a side opening or aperture by inserting the connecting part and the sheet into the vessel through its opening and pulling gently on the prosthesis to apply the sheet against the inside wall of the vessel around its opening, the free end of the sheet being in the immediate vicinity of the periphery of the opening in the vessel.

Thus, around the opening, the vessel wall is to some degree doubled on the inside by the sheet.

It is then easy to join the sheet to this vessel wall by pinching them together, for example by clips which are small staples engaged to straddle the vessel wall and the sheet after which the wall and the sheet are brought tightly together by bringing together the two legs of each staple by plastic deformation.

In another embodiment, the sheet is located inside the connecting part.

In this embodiment, the sheet is joined to the vessel wall from the inside of the prosthesis, which can be done only if the prosthesis has a passage, other than its opening, for access to its interior.

In a second embodiment, the prosthesis according to the invention is used to create an end-to-end anastomosis.

In this case it has an annular sheet in the shape of a cylindrical section, taken between two planes perpendicular to the axis of this cylinder, and with a diameter substantially equal to that of the vessel to be treated.

The sheet preferably extends around the end of the prosthesis, in the manner of a sleeve, and is joined to the end at its opening, while the free end of the sheet is placed around the prosthesis, at a distance from the opening.

Such a prosthesis is installed simply by inserting it into the blood vessel until the free edge of the sheet abuts the end opening in the vessel.

The sheet is then applied to the inside wall of the vessel.

To join the prosthesis to the vessel, one need only pinch the vessel wall and the sheet together, for example by placing the above-described clips all around the opening.

In one embodiment, the sheet extends not around but inside the end of the prosthesis, being joined to the latter at the opening, the free edge of the sheet being at a distance from the opening, inside the prosthesis.

Such a prosthesis is installed by capping the end of the vessel until the free edge of the sheet reaches the end opening in the vessel.

As described above, the vessel wall and the sheet are then joined by pinching them together. This makes it necessary to operate from inside the prosthesis, which is not impossible since the joining means used, namely the clips for example, can be installed in a very small working space, hence in particular inside the prosthesis itself.

Of course, in this case, the prosthesis must, at the time of the operation, have a passage different from the opening into which the clips and surgical instruments can be inserted.

BRIEF DESCRIPTION OF THE DRAWINGS

For better understanding of the invention, a number of embodiments will now be described with reference to the attached drawing wherein:

FIG. 7 is a perspective view of an alternative prosthesis according to the first embodiment of the invention;

FIG. 8 represents a prosthesis according to a second embodiment of the invention before it is installed in a blood vessel;

FIG. 9 is a cross-sectional view of FIG. 8;

FIG. 10 is a detailed view of FIG. 9, with the prosthesis joined to the vessel;

FIG. 11 is an exterior view of FIG. 10 after the anastomosis of the prosthesis to the vessel;

FIG. 12 is a cross-sectional view showing another variant of the first embodiment of the invention; and FIG. 13 is a cross-sectional view showing another variant of the second embodiment of the invention.

DETAILED DESCRIPTION OF PREFERRED EMBODIMENTS

Figure 1:
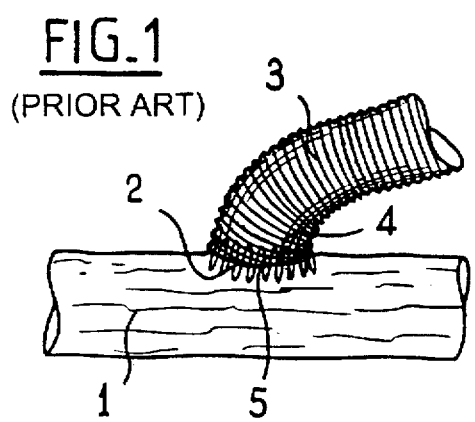
FIG. 1 illustrates the prior art.

FIG. 1 shows an artery 1 in which a lateral hole 2 is created.

A vascular prosthesis 3 is anastomosed to artery 1 by edge-suturing of the substantially elliptical opening 4 in the prosthesis and the hole 2 in the artery with the aid of a thread 5.

This anastomosis technique corresponds to the prior art.

Figure 2:
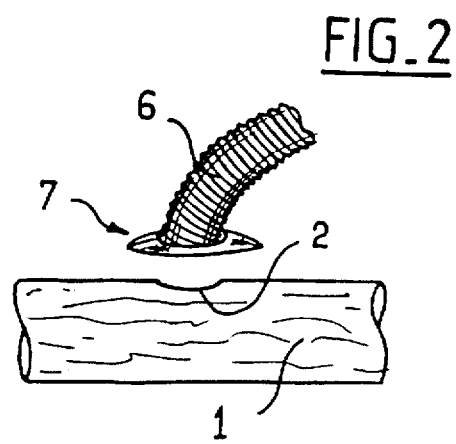
FIG. 2 represents the end of a prosthesis according to a first embodiment of the invention about to be installed in a blood vessel.

FIG. 2 shows an artery 1 identical to the foregoing, with its lateral hole 2.

A prosthesis 6 according to a first embodiment is shown opposite hole 2 to be anastomosed to artery 1.

Figure 3:
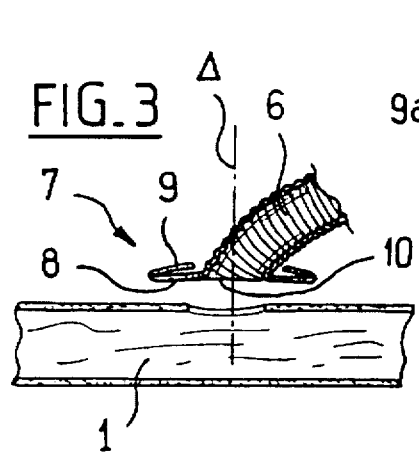
FIG. 3 is a cross-sectional view of FIG. 2.

Prosthesis 6 has at its end 7 means for joining it to artery 1 which are more clearly visible in FIG. 3.

The means have a connecting part 8 extending from the wall of the prosthesis 6 continuously and an annular sheet 9 which, in the present case, is an extension, folded back on itself, of connecting part 8.

Connecting part 8 and annular sheet 9 extend all around opening 10 in the prosthesis and are shaped like part of a cylinder.

Figure 3A:
FIG. 3A is a detailed view of FIG. 3.

FIG. 3A shows annular sheet 9 considered in isolation, which indeed has the shape of a side portion of a cylinder delimited interiorly by an edge 9a and exteriorly by an edge 9b.

In the sense of the invention, edge 9a is the free edge of the sheet. Viewed along axis Δ of opening 10 in the prosthesis, edge 9a has a substantially elliptical shape.

Edge 9b is the peripheral edge of the sheet.

In this example, connecting part 8 and annular sheet 9 are made of the same material as the rest of the prosthesis, from an end thermoformed from the latter, but it is clear that they could be made separately then joined to the prosthesis by gluing or welding, the essential condition to be met being that the joint between the annular part 9 and the rest of the prosthesis be continuous, namely have no orifices.

Figure 4:
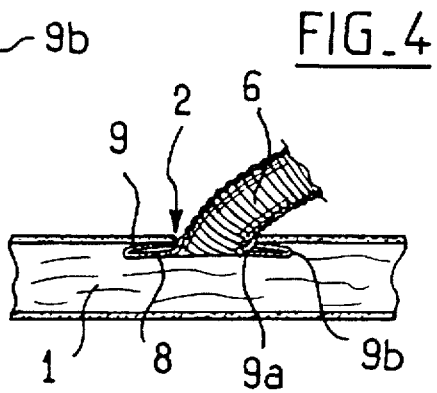
FIG. 4 is a cross-sectional view analogous to FIG. 3, after positioning of the prosthesis.

As can be seen in FIG. 4, the prosthesis is installed by inserting connecting part 8 and annular sheet 9 into hole 2, then pulling gently on the prosthesis to apply said annular sheet 9 against the inside wall of the artery, around hole 2.

Free edge 9a is then in the vicinity of the periphery of the hole.

Figure 5:
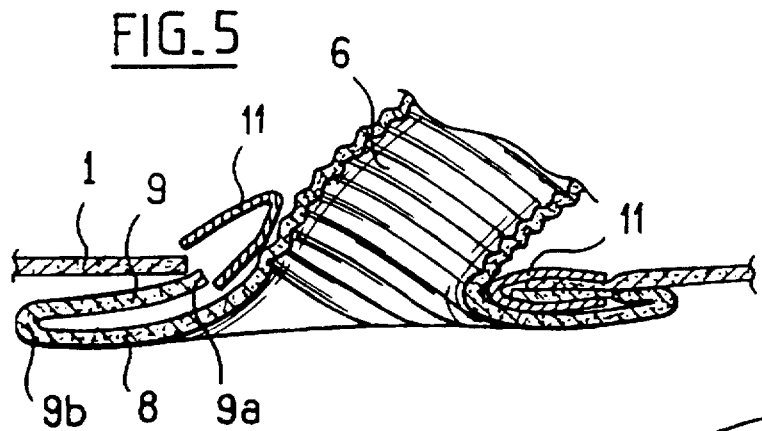
FIG. 5 is a detailed view of FIG. 4 when the prosthesis is joined to the vessel.
Figure 6:
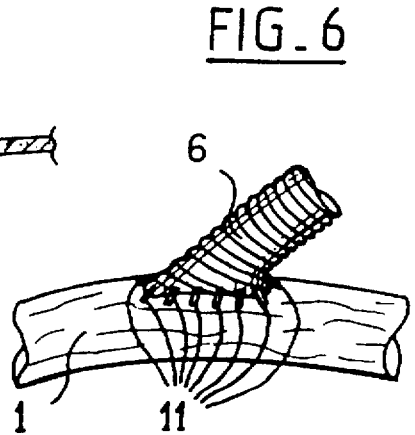
FIG. 6 is an exterior view of the anastomosed vessel and prosthesis.

It then remains to join the prosthesis to the artery, which can be done with clips 11 of the type shown in FIG. 5.

Clips can easily be inserted to straddle the wall of vessel 1 and annular sheet 9, as shown at the left of FIG. 5, then squeezed to pinch them together, as shown on the right of FIG. 5.

In this way, clips 11 are disposed all around hole 2 in a sufficient quantity to ensure a good join of the prosthesis to the artery.

FIG. 7 shows a prosthesis 12 intended, like that of the previous embodiment, to be joined laterally to a blood vessel but which, unlike the foregoing, connects to this vessel perpendicularly rather than obliquely.

For this reason, opening 13 in the prosthesis is not elliptical but substantially circular.

The prosthesis then has an annular sheet 14 which, viewed along axis Δ' of opening 13, is circular in shape.

In fact, as previously shown, annular sheet 14 is part of a cylinder of the type shown in FIG. 3A, which means that it has the shape of a ring resting on the side wall of a cylinder.

FIG. 8 shows a second embodiment of the invention in which a prosthesis 15, designed for an end-to-end anastomosis, is placed opposite an artery 16 terminating in an opening 16a.

The prosthesis has an annular sheet 17 which, in this example, is made of the same material as the rest of the prosthesis, and is simply an end portion folded exteriorly, as seen in FIG. 9.

Free edge 17a of annular sheet 17 is located around the prosthesis.

The outer diameter of annular sheet 17 is substantially equal to or slightly less than the inside diameter of artery 16 to be treated.

The prosthesis is installed by inserting its annular sheet 17 inside artery 16 until its free edge 17a is next to the periphery of opening 16a, as shown in FIG. 10, then the prosthesis is joined to the artery with the aid of clips 11, identical to those described previously.

FIG. 11 shows the prosthesis and the artery after the anastomosis has been created.

FIG. 12 shows a variant of the embodiment in FIGS. 2 to 6.

In this variant, annular sheet 9' of prosthesis 6' is not located outside connecting part 8' but inside the latter.

The prosthesis is then installed on the artery merely by resting it against the outside wall of the vessel, after opening 10' in the prosthesis has been aligned with lateral hole 2 in the artery.

The artery wall is then joined to annular sheet 9' by installing clips (not shown) similar to clips 11 described above, but this time from the inside of the prosthesis.

These clips can be positioned and tightened for example by endoscopy inside the prosthesis.

FIG. 13 shows a variant of the embodiment of FIGS. 8 to 11.

In this variant, annular sheet 17' of prosthesis 15' is not located outside but inside the prosthesis.

Such a prosthesis is installed by causing it to cap the end of artery 16 to be treated, then joining annular sheet 17' to the vessel wall by installing clips (not shown) from the inside of the prosthesis.

The variants of FIGS. 12 and 13 may be indicated when it is desired to treat blood vessels whose diameters are inadequate to support the presence of annular sheet 9 or 16 interiorly.

In FIGS. 12 and 13, the same reference numerals are used as above plus the prime to designate the same elements.

Of course, the embodiments described are not limiting in nature and may receive any desirable modifications without thereby departing from the framework of the invention.

In particular, it should be noted that, although the invention has been described in relation to a prosthesis anastomosed to a natural blood vessel, it also relates to a prosthesis that can be anastomosed to another prosthesis, which also constitutes a pipe in the sense of the present invention, in the same way as a natural blood vessel.

What is claimed is:

1. A vascular prosthesis capable of being anastomosed onto a tubular pipe provided with a side opening or end opening, the prosthesis comprising:

an annular sheet on at least one end of the prosthesis, the sheet delimited by a free edge designed to be positioned in the immediate vicinity of the opening in the pipe, wherein said sheet is shaped so that it can be applied around the opening in the pipe against the inside or outside wall of the pipe, while preserving its free edge in the immediate vicinity of the periphery of the opening in the pipe.

2. The prosthesis according to claim 1, designed to create a side-to-end anastomosis, wherein the annular sheet is in the shape of a side part of a cylinder, delimited exteriorly by a peripheral edge corresponding substantially to the intersection of this cylinder with another cylinder, and delimited interiorly by its free edge which defines an orifice corresponding to the opening in the prosthesis.

3. The prosthesis according to claim 2, wherein the annular sheet is connected to the end of the prosthesis by a connecting part which starts at the end of the prosthesis and extends up to the peripheral edge of the sheet, said connecting part having substantially the same shape as the sheet so that the free end of the sheet is located in the vicinity of the beginning of the connecting part, at the end of the prosthesis.

4. The prosthesis according to claim 2, wherein the sheet is located outside the connecting part such that the end of the prosthesis passes through the orifice delimited by free edge of the sheet and extends radially by the connecting part up to the peripheral edge of the sheet, which covers the connecting part.

5. The prosthesis according to claim 2, wherein the sheet is located inside connecting part.

6. The prosthesis according to claim 1, designed to create an end-to-end anastomosis, wherein the prothesis has an annular sheet in the shape of a section of a cylinder between two planes perpendicular to the axis of this cylinder, and with a diameter substantially equal to that of the vessel to be treated.

7. The prosthesis according to claim 6, wherein the sheet extends around the end of the prosthesis in the manner of a sleeve, being joined to the end at the opening of the prosthesis, while the free edge of the sheet is located around the prosthesis, at a distance from the opening in the prosthesis.

8. The prosthesis according to claim 6, wherein the sheet extends inside the end of the prosthesis being joined to the prosthesis at the opening in the prosthesis, the free end of the sheet being at a distance from the opening of the prosthesis.

* * * * *